| United States Patent [19] | [11] | 4,404,143 |
|---|---|---|
| Sekiguchi et al. | [45] | Sep. 13, 1983 |

[54] PROCESS FOR PRODUCING HIGH CONCENTRATION SOLUTION OF SALT OF ALPHA-SULFO FATTY ACID ESTER

[75] Inventors: Shizuo Sekiguchi; Yozo Miyawaki; Toshiaki Ogoshi, all of Funabashi, Japan

[73] Assignee: Lion Corporation, Tokyo, Japan

[21] Appl. No.: 274,478

[22] Filed: Jun. 16, 1981

[30] Foreign Application Priority Data

Jun. 16, 1980 [JP] Japan ................................ 55-80119

[51] Int. Cl.$^3$ ........................................ C07C 139/14
[52] U.S. Cl. .................................... 260/400; 560/149
[58] Field of Search ......................... 260/400; 560/149

[56] References Cited

U.S. PATENT DOCUMENTS

| 2,878,271 | 3/1959 | Little et al. | 260/400 |
| 3,024,258 | 3/1962 | Brooks et al. | 260/400 |
| 3,230,244 | 1/1966 | Stirton et al. | 260/400 X |
| 3,354,187 | 11/1967 | Stein et al. | 260/400 |
| 3,919,125 | 11/1975 | Ashima et al. | 260/458 X |
| 3,997,575 | 12/1976 | Ogoshi et al. | 260/400 |
| 3,997,576 | 12/1976 | Ogoshi et al. | 260/410.9 R |
| 4,261,917 | 4/1981 | Hayashi et al. | 260/458 R |

*Primary Examiner*—Thomas A. Waltz
*Attorney, Agent, or Firm*—Armstrong, Nikaido, Marmelstein & Kubovcik

[57] ABSTRACT

A high concentration aqueous solution of the salt of an alpha-sulfo fatty acid ester is produced by (a) neutralizing the sulfonated product of a fatty acid ester with an aqueous caustic alkali solution having a concentration of 15 through 50% by weight, in the presence of an alcohol having 1 to 4 carbon atoms in an amount of 5 through 20% by weight based on the weight of the sulfonated product, to form an acidic neutralized product having a pH of 2.5 through 4 and; then, (b) adding an aqueous caustic alkali solution having a concentration of 1 through 5% by weight to the acidic neutralized product to adjust the pH of the acidic neutralized product to 6 through 7. The aqueous solution of the salt of the alpha-sulfo fatty acid ester thus obtained includes only small amounts of the undesired alpha-sulfo fatty acid salt.

7 Claims, No Drawings

PROCESS FOR PRODUCING HIGH CONCENTRATION SOLUTION OF SALT OF ALPHA-SULFO FATTY ACID ESTER

BACKGROUND OF THE INVENTION

1. Field of the Invention

This invention relates to a process for producing a high concentration aqueous solution of the salt of an alpha-sulfo fatty acid ester. More specifically it relates to a process for producing an aqueous solution containing a low concentration of the salt of an alpha-sulfo fatty acid and a high concentration of the salt of an alpha-sulfo fatty acid ester.

2. Description of the Prior Art

It is known in the art that an aqueous solution of the salt of an alpha-sulfo fatty acid ester can be produced by first sulfonating a fatty acid ester and, then, neutralizing the resultant sulfonated product with an aqueous caustic alkali solution, desirably after bleaching. It is also known in the art that the ester linkage tends to be cleaved during the sulfonation, bleaching and neutralization steps of this production process. The cleavage of the ester linkage necessarily causes the by-production of the salt of alpha-sulfo fatty acid. However, the salt of alpha-sulfo fatty acid is only slightly soluble in water and, also, has poor surface activity. Therefore, the inclusion of the by-product alpha-sulfo fatty acid salt in the aqueous solution of the salt of the alpha-sulfo fatty acid ester is not desired in the art.

Various attempts to prevent the cleavage of the ester linkage and to suppress the by-production of the undesired alpha-sulfo fatty acid salt have been proposed in the art. However, most of these proposals are concerned with improvements in the sulfonation or bleaching step and improvements in the neutralization step have scarcely been tried. The only improvement in the neutralization step is that the neutralization is carried out under relatively mild conditions to inhibit the cleavage (or hydrolysis) of the ester linkage during the neutralization step.

As is known, a high concentration is generally desired in the aqueous solution of a surface active agent. This is also true in the aqueous solution of the salt of an alpha-sulfo fatty acid ester. In the case where the concentration of the aqueous solution of the salt of an alpha-sulfo fatty acid ester is low, there is a disadvantage in the storage and the transportation thereof. The high concentration aqueous solution of the salt of an alpha-sulfo fatty acid ester can be theoretically obtained by concentrating from the low concentration aqueous solution or neutralizing the sulfonated products of a fatty acid ester with an high concentration alkali-solution. However, the former method is not recommended due to the fact that the content of the undesired alpha-sulfo fatty acid salt is increased by heating during concentration. On the other hand, the neutralization of the sulfonated fatty acid ester by using a high concentration aqueous caustic alkali solution has a disadvantage in that, since the viscosity of the solution is rapidly increased in the course of the neutralization step (even in the case where a relatively dilute aqueous caustic alkali solution is used), uniform agitation becomes difficult. As a result, an excessive alkaline region is locally formed in the aqueous solution to be neutralized and, therefore, the ester linkage is generally hydrolyzed. Thus, in the case where an aqueous caustic alkali solution having a high concentration is used, the undesirable hydrolysis of the ester linkage is accelerated. Accordingly, the use of a high concentration aqueous caustic alkali solution in the neutralization of the sulfonated fatty acid ester is not recommended.

As mentioned hereinabove, the production of an aqueous solution of the salt of an alpha-sulfo fatty acid ester containing a high concentration of the salt of an alpha-sulfo fatty acid ester (i.e. a desired surface active agent), but a low concentration of the salt of an alpha-sulfo fatty acid (i.e. an undesired impurity) is extremely difficult in the prior art.

SUMMARY OF THE INVENTION

The object of this invention is to obviate the above mentioned problems of the conventional processes for producing an aqueous solution of the salt of an alpha-sulfo fatty acid ester. More specifically, the object of the present invention is to produce a high concentration aqueous solution of the salt of an alpha-sulfo fatty acid ester containing, as an impurity, the salt of the alpha-sulfo fatty acid at a low concentration.

Other objects and advantages of the present invention will be apparent from the description set forth hereinbelow.

In accordance with this invention, there is provided a process for producing a high-concentration aqueous solution of the salt of an alpha-sulfo fatty acid ester comprising the steps of:

(a) neutralizing the sulfonated product of a fatty acid ester with an aqueous caustic alkali solution having a concentration of 15 through 50% by weight, in the presence of an alcohol having 1 to 4 carbon atoms in an amount of 5 through 20% by weight based on the weight of the sulfonated product, to form an acidic neutralized product having a pH of 2.5 through 4 and; then, (b) adding an aqueous caustic alkali solution having a concentration of 1 through 5% by weight to the acidic neutralized product to adjust the pH of the acidic neutralized product to 6 through 7.

DESCRIPTION OF THE PREFERRED EMBODIMENTS

Prior to the detailed description of the neutralization step, which is important for the production of the desired high concentration solution of the salt of an alpha-sulfo fatty acid ester, the sulfonation of the fatty acid esters now will be described in detail.

The fatty acid esters used in the process according to this invention preferably include those which are derived from fatty acids having 10 to 24 carbon atoms and alcohols having 1 to 4 carbon atoms, because the resultant final solution of this invention should be used as a surface active agent. Either linear fatty acids or branched fatty acids can be used as an acid component in this invention. Examples of the typical fatty acid esters are methyl caprate, methyl laurate, ethyl laurate, methyl myristate, propyl myristate, methyl palmitate, ethyl palmitate, methyl stearate, ethyl stearate, ethyl arackate, methyl behenate, methyl lignocerate, hardened coconut oil fatty acid methyl ester, hardened tallow fatty acid methyl ester, hardened palm oil fatty acid methyl ester and the like. These fatty acid esters can be used alone or in any mixture thereof.

The sulfonation of the fatty acid esters can be typically carried out by using sulfur trioxide ($SO_3$) as a sulfonating agent. The sulfonation can be carried out in either a continuous or a batchwise manner, but the sulfonation conditions under which no substantial cleavage of the ester linkage occurs should be selected. Those conditions can be easily determined by those skilled in the art. For example, fatty acid esters are sulfonated by using $SO_3$ gas diluted with an inert gas (e.g. nitrogen or air) to 0.5 through 20% by volume, as a sulfonating agent, at a mol ratio of $SO_3$ to the fatty acid esters of 0.9 through 1.5 and a temperature of about 30° through about 100° C. Since the sulfonation reaction of the fatty acid esters proceeds in two stages, the resultant reaction mixture is desirably aged at a temperature of about 30° through about 100° C.

The sulfonated fatty acid esters as prepared above can be directly subjected to a neutralization step. However, the sulfonated fatty acid esters are desirably and advantageously bleached prior to the neutralization. This is because not only the bleaching is effective for improving the color of the final solution of the salts of alpha-sulfo fatty acid esters but also the subsequent neutralization step can be desirably affected. Although any conventional bleaching technique can be used, the sulfonated fatty acid esters can be preferably bleached by using hydrogen peroxide in the presence of an alcohol having 1 to 4 carbon atoms at a temperature of 50° through 100° C. The amounts of hydrogen peroxide and alcohol used in the bleaching of the sulfonated fatty acid esters are usually 0.5 through 10 parts by weight and 1 through 20 parts by weight, based on 100 parts by weight of the sulfonated fatty acid esters, respectively. The hydrogen peroxide can be used in the form of an aqueous solution thereof having a concentration of 10% by weight or more. As an alcohol which should be present in the bleaching system, methanol can be advantageously used when the fatty acid esters are methyl esters, and ethanol can be advantageously used when the fatty acid esters are ethyl esters.

The sulfonated fatty acid esters, preferably after being subjected to the bleaching treatment, are neutralized in the subsequent neutralization step of this invention. As mentioned hereinabove, the sulfonated fatty acid esters are neutralized by using an aqueous caustic alkali solution having a relatively high concentration, that is, 15 through 50% by weight in the presence of an alcohol having 1 to 4 carbon atoms in an amount of 5 through 20% by weight based on the weight of the sulfonated fatty acid esters. That is, the sulfonated fatty acid esters and the aqueous caustic alkali solution are uniformly mixed with each other until the pH of the mixture becomes 2.5 through 4. Thus, the acidic neutralized product is obtained.

It has been found that all of the alpha-sulfo fatty acid esters can be substantially neutralized and converted to the salts of the alpha-sulfo fatty acid esters in the neutralized products having a pH of 2.5 through 4 and also that the ester linkages are not hydrolyzed and the mixture of the alpha-sulfo fatty acid esters and the aqueous caustic alkali solution is kept in such a low viscosity that thorough and uniform mixing of the mixture can be effected throughout the neutralization step until the pH of the mixture becomes 2.5 through 4. It is considered that this is because the inorganic substances are not neutralized and the content of inorganic salts is very low. If the pH of the neutralized mixture is less than 2.5, the viscosity is kept very low but the cleavage of ester linkage occurs by acidity. Contrary to this, if the pH of the neutralized product is more than 4, the viscosity increases and uniform mixing can not be effected and hence the cleavage of ester linkage occurs.

The neutralization step of this invention should be carried out in the presence of an alcohol having 1 to 4 carbon atoms in an amount of 5 through 20% by weight based on the weight of the sulfonated fatty acid esters. The alcohol should be added to the neutralization reaction system prior to the initiation of the neutralization reaction. Even in the case where an alcohol having 1 to 4 carbon atoms is present in the sulfonated product to be neutralized (e.g. the alcohol used in the optional bleaching step remains in the sulfonated product), the alcohol necessary to effect the neutralization of this invention should be added to the neutralization system. The alcohols used in the neutralization step can be any aliphatic alcohols having 1 to 4 carbon atoms. Examples of such alcohols are methanol, ethanol, n-propanol, iso-propanol, n-butanol, sec-butanol, ter-butanol and the like. These alcohols can be used alone or in any mixture thereof. However, the use of alcohol, which is the same as the alcohol component of the fatty acid ester to be neutralized, is recommended. For instance, the use of methanol in the case of the methyl ester and the use of ethanol in the case of the ethyl ester is desirable.

The aqueous caustic alkali solution used in the neutralization step should have a concentration of 15 through 50% by weight. In the case where the concentration of the aqueous caustic alkali solution is less than 15% by weight, the viscosity of the mixture under neutralization increases during the course of the neutralization and uniform stirring of the mixture becomes difficult. As a result, an excessive alkaline region locally appears in the mixture under neutralization, so that the undesirable hydrolysis of the ester linkage occurs. Contrary to this, in the case where the concentration of the aqueous caustic alkali solution is more than 50% by weight, the viscosity of the mixture under neutralization increases and the uniform mixing becomes difficult. Typical examples of caustic alkali are sodium hydroxide, potassium hydroxide, magnesium hydroxide, magnesium oxide, barium hydroxide, calcium hydroxide and the like. These caustic alkalis can be used alone or in any mixture thereof. The suitable neutralization temperature is within the range of from 30° to 80° C., although the scope of this invention is not limited to this temperature range.

According to this invention, the pH of the acidic neutralized products having a pH of 2.5 through 4 obtained in the neutralization step are then adjusted to a pH of 6 through 7 by using a 1 through 5% by weight aqueous caustic alkali solution. If the pH of the acidic neutralized product is not adjusted to a pH of 6 through 7, the salts of the alpha-sulfo fatty acid esters are hydrolyzed during the storage thereof to form the salts of the corresponding alpha-sulfo fatty acids as a by-product. The aqueous caustic alkali solutions used in the pH adjusting step can be the same as or different from those used in the above-mentioned neutralization step. Generally, a dilute aqueous solution of sodium hydroxide or potassium hydroxide is conveniently used. However, in the case where the concentration of the aqueous caustic alkali solution is too low, the concentration of the final aqueous solution of the salt of the alpha-sulfo fatty acid ester is undesirably decreased. Contrary to this, in the case where the concentration of the aqueous caustic alkali solution is too high, the undesirable cleavage of the ester linkage occurs during the pH adjusting step. Thus, the concentration of the aqueous caustic alkali solution used in the pH adjusting step should be within the range of from 1 to 5% by weight. The suitable pH adjusting temperature is within the range of from 30° to 80° C., although the scope of this invention is not limited to this temperature range.

As explained hereinbefore, a high concentration aqueous solution of the salt of an alpha-sulfo fatty acid ester having a concentration of 50 through 65% by weight can be advantageously produced in accordance with the neutralizing step and the subsequent pH adjusting step of this invention. Although the ester salt solution is produced through the neutralization step in which a relatively high concentration caustic alkali solution is used, the desired aqueous solution of the salt of an alpha-sulfo fatty acid ester having a high purity (e.g. 95% or more) and containing a small amount of the salt of the alpha-sulfo fatty acid ester (e.g. 5% or less) can be obtained. This is because the hydrolysis of the ester linkage can be effectively prevented since the neutralization is carried out in the presence of the lower alcohol.

Furthermore, in the case where the sulfonated fatty acid esters are bleached with hydrogen peroxide prior to the neutralization step, the resultant hydrogen peroxide is decomposed during the neutralization step and, therefore, the color of the solution is further improved.

EXAMPLES

This invention now will be further illustrated by the following examples. However, it should be noted that these examples are presented merely to explain and not to limit the invention, and that numerous changes may be made without departing from the spirit and the scope of this invention as hereinafter claimed.

The sulfonated fatty acid esters used in the following examples were prepared as follows.

Into a vessel type reactor provided with a gas feed pipe, a thermometer and an agitator, 2900 parts by weight of extremely hardened tallow fatty acid methyl ester having an average molecular weight of 290 was charged and heated to a temperature of 80° C. with stirring. 1040 parts by weight of 5% by volume of sulfur trioxide gas diluted with nitrogen gas (1.3 mols of sulfur trioxide per 1 mol of the ester) was introduced into the ester liquid over 60 mins. with stirring and, then, the reaction mixture was aged at a temperature of 80° C. for 20 mins. Thus, the sulfonated product A was obtained.

500 parts by weight of the sulfonated product A was placed in a vessel provided with an agitator. 75 parts by weight of methanol and 21.4 parts by weight of 35% hydrogen peroxide (i.e. 7.5 parts by weight in terms of $H_2O_2$) were added to the vessel and the sulfonated product A and bleached at a temperature of 80° C. for 60 mins. with stirring. Thus, the sulfonated product B was obtained.

The sulfonated products C and D were prepared from the sulfonated product A in a manner as described in the preparation of the sulfonated product B, except that the bleaching conditions were changed as shown in Table 1 below.

Furthermore, the sulfonated products E and F were prepared in a manner as described in the preparation of the sulfonated product B, except that extremely hardened plam oil fatty acid methyl ester and methyl stearate were used, respectively, instead of the hardened tallow fatty acid methyl ester.

The production conditions and properties of the sulfonated products A through F are summarized in Table 1 below.

TABLE 1

| Sulfonated Product No. | A | B | C | D | E | F |
|---|---|---|---|---|---|---|
| Production Conditions | | | | | | |
| $SO_3$/Fatty Acid Ester (molar ratio) | 1.3 | 1.3 | 1.3 | 1.3 | 1.3 | 1.3 |
| Sulfonation Temperature (°C.) | 80 | 80 | 80 | 80 | 80 | 80 |
| Bleaching Conditions | | | | | | |
| Addition Amount of $H_2O_2$ (%) | — | 1.5 | 1.5 | 1.5 | 1.5 | 1.5 |
| Addition Amount of Methanol (%) | — | 1.5 | 30 | — | 15 | 15 |
| Bleaching Temperature (°C.) | — | 80 | 80 | 80 | 80 | 80 |
| Properties | | | | | | |
| Sulfonation Conversion*1 (%) | 98.3 | 98.3 | 98.5 | 98.4 | 97.8 | 97.6 |
| Color*2 | 3000 | 100 | 250 | 2100 | 50 | 120 |
| Ester Content*3 (%) | 81.5 | 100 | 100 | 54.5 | 100 | 100 |

(Remarks)
*1 The sulfonation conversion was determined according to a petroleum ether extraction method.
*2 The color was expressed as $(-\log T) \times 10^3$ after determining absorbance (T) of light having a wavelength of 420 nm through 5% ethanol solution.
*3 The ester content was determined by separately weighing the salt of alpha-sulfo fatty acid ester and the salt of alpha-sulfo fatty acid, after separating them by utilizing the difference in the solubility thereof in hydrous ethanol. The ratio of the ester in the active ingredient was calculated as the ester content.

EXAMPLE 1

The sulfonated products A through D of the hardened tallow fatty acid were neutralized under various neutralizing conditions as listed in Table 2 below. Thus, aqueous solutions of the sodium salts of the alpha-sulfo extremely hardened tallow fatty acid methyl esters were obtained. The inflexion point of each titration curve of the sulfonated products A through D appeared in the neighborhood of pH=3.5. Therefore, the addition amount of the sodium hydroxide for neutralization was determined from the amount of the sodium hydroxide by which the sulfonated product was neutralized to the inflexion point.

The calculated amounts of aqueous caustic soda solutions having various concentrations were weighed into vessels and heated to a temperature of 40° C. A uniform mixture 100 parts by weight each of the sulfonated products A through D and a predetermined amount of methanol was added to the aqueous caustic soda solution and neutralized by vigorous stirring. The temperature of the neutralized mixture after the completion of the neutralization was within the range of from 50° to 55° C.

Except for the neutralized product of Run No. 2 having a substantially neutral pH, after cooling the neutralized product to a temperature of from 50° through 55° C., a 5 or 12% aqueous caustic soda solution was gradually added to the neutralized product over 30 minutes with thorough stirring to adjust the pH of the neutralized product to about 6.5.

The neutralizing and pH adjusting conditions and properties of the neutralized products and final products are shown in Table 2 below. The ester contents, the sulfonation conversions and the color were determined in the same manner as in the sulfonated products.

TABLE 2

| | Run No. | | | | | | | | |
|---|---|---|---|---|---|---|---|---|---|
| | 1 | 2* | 3 | 4* | 5* | 6 | 7* | 8 | 9 |
| Type of Sulfonated Product | A | | B | | | | C | | D |
| Neutralization | | | | | | | | | |
| Concentration of NaOH (%) | 18 | 22 | 25 | 25 | 20 | 48 | 22 | 30 | 18 |
| Addition Amount of NaOH (parts) | 71 | 50 | 42.8 | 42.8 | 53.6 | 22.3 | 44.5 | 32.8 | 71 |
| Addition Amount of Methanol | 15 | 15 | 15 | 15 | — | 15 | — | 15 | 15 |
| Concentration of NaOH (%) used in pH adjusting | 5 | — | 5 | 12 | 5 | 5 | 5 | 5 | 5 |
| Property | | | | | | | | | |
| pH of Neutralized Product | 3.7 | 6.5 | 5 | 3.5 | 3.5 | 3.5 | 3.5 | 3.5 | 3.5 |
| pH of Final Product | 6.3 | | 6.5 | 6.5 | 6.5 | 6.5 | 6.3 | 6.3 | 6.5 |
| Viscosity of Neutralized Product (poise) | 2–3 | 12 | 1–2 | 1–2 | 25–30 | 25–28 | — | about 1 | 2–3 |
| Viscosity of Final Product (poise) | 20 | | 15 | 13 | 300 | 200–250 | 60–70 | 10 | 20–25 |
| Concentration of Active Component in Neutralized Product (%) | 52.6 | 50.1 | 52.0 | 51.9 | 53.4 | 60.1 | 52.0 | 51.1 | 52.3 |
| Concentration of Active Component in Final Product (%) | 51.0 | | 50.1 | 51.2 | 51.4 | 57.6 | 50.1 | 49.2 | 51.2 |
| Ester Content of Neutralized Product (%) | 81.4 | 83.5 | 100 | 100 | 74.1 | 98.8 | 90.5 | 100 | 54.1 |
| Ester Content of Final Product (%) | 81.3 | | 100 | 89.5 | 74.0 | 98.6 | 90.4 | 100 | 53.8 |
| Sulfonation Conversion (%) | 98.3 | 98.3 | 98.3 | 98.3 | 98.3 | 98.3 | 98.5 | 98.5 | 98.4 |
| Color | 2920 | 60 | 60 | 60 | 85 | 55 | 160 | 125 | 1750 |

*Comparative Experiment

As is clear from the results shown in Table 2, in the case where the sulfonation product was neutralized at one stage to a pH of 6.5 as in Run No. 2, the content of the ester was decreased by the hydrolysis. In the case where no methanol was added during the neutralization step as in Run No. 5 or 7, the content of the ester was decreased due to the occurrence of the hydrolysis of the ester linkage although the sulfonated product was neutralized to the inflexion point. Furthermore, in the case where a diluted aqueous caustic alkali solution was not used in the pH adjusting step as in Run No. 4, the content of the ester was decreased due to the occurrence of the hydrolysis of the ester linkage.

Contrary to the above, no substantial hydrolysis of the ester linkage occurred in the neutralization step in Run Nos. 1, 3, 6, 8 and 9 according to the present invention. Especially when the sulfonated product having a high ester content was used as in Run Nos. 3, 6 and 8, the content of di sodium salt of alpha-sulfo extremely hardened tallow fatty acid was very low (less than 2%). Therefore these final products can be preferably used as a surface active agent.

EXAMPLE 2

A uniform mixture of 100 parts by weight of the sulfonated product E of the hardened palm oil fatty acid methyl ester and 15 parts by weight of methanol was added to 47.4 parts by weight of 23% aqueous caustic soda solution at 40° C. and neutralized with vigorous stirring. The temperature of the neutralized mixture was raised to 60° through 65° C. The properties of the neutralized product were as follows.

| pH: | about 3.5 |
|---|---|
| Ester Content: | 99.5% |
| Concentration of Active Component: | 50.2% |

The neutralized product thus obtained was cooled to 50° through 55° C. and, then, 5% aqueous caustic soda solution was gradually added to the neutralized product over 30 minutes to adjust the pH of the neutralized product to about 6.5. The properties of the resultant final product were as follows.

| Concentration of Active Component: | 48.4% |
|---|---|
| Ester Content: | 99.5% |
| Sulfonation Conversion: | 97.8% |
| Color: | 18 |

EXAMPLE 3

A uniform mixture of 100 parts by weight of the sulfonated product F of the methyl stearate and 15 parts by weight of methanol was added to 45.8 parts by weight of 23% aqueous caustic soda solution at 40° C. and neutralized with vigorous stirring. The temperature of the neutralized mixture was raised to 60° through 65° C. The properties of the neutralized product were as follows.

| pH: | about 3.5 |
|---|---|
| Ester Content: | 100% |
| Concentration of Active Component: | 50.6% |

The neutralized product thus obtained was cooled to 50° through 55° C. and, then, 5% aqueous caustic soda solution was gradually added to the neutralized product over 30 minutes to adjust the pH of the neutralized product to about 6.5. The properties of the resultant final product were as follows.

| Concentration of Active Component: | 49.0% |
|---|---|
| Ester Content: | 100% |
| Sulfonation Conversion: | 97.6% |
| Color: | 71 |

I claim:

1. A process for producing a high-concentration aqueous solution of the salt of an alpha-sulfo fatty acid ester comprising the steps of:
   (a) neutralizing the sulfonated product of a fatty acid ester with an aqueous caustic alkali solution having a concentration of 15 through 50% by weight, in the presence of an alcohol having 1 to 4 carbon atoms in an amount of 5 through 20% by weight based on the weight of the sulfonated product, to form an acidic neutralized product having a pH of 2.5 through 4 and; then, (b) adding an aqueous caustic alkali solution having a concentration of 1 through 5% by weight to the acidic neutralized product to adjust the pH of the acidic neutralized product to 6 through 7.

2. A process as claimed in claim 1, wherein the sulfonated product of the fatty acid ester is the sulfonated product of a fatty acid having 10 to 24 carbon atoms and an alcohol having 1 to 4 carbon atoms.

3. A process as claimed in claim 1, wherein the fatty acid ester is at least one selected from the group consisting of methyl caprate, methyl laurate, ethyl laurate, methyl myristate, propyl myristate, methyl palmitate, ethyl palmitate, methyl stearate, ethyl stearate, ethyl arackate, methyl behenate, methyl lignocerate, hardened coconut oil fatty acid methyl ester, hardened tallow fatty acid methyl ester and hardened palm oil fatty acid methyl ester.

4. A process as claimed in claim 1, wherein the alcohol is at least one selected from the group consisting of methanol, ethanol, n-propanol, iso-propanol, n-butanol, sec-butanol and ter-butanol.

5. A process as claimed in claim 1, wherein the alcohol is added to the neutralization reaction system prior to the initiation of the neutralization reaction.

6. A process as claimed in claim 1, wherein the caustic alkali is at least one selected from the group consisting of sodium hydroxide, potassium hydroxide, magnesium hydroxide, magnesium oxide, barium hydroxide and calcium hydroxide.

7. A process as claimed in claim 1, wherein the concentration of the aqueous solution of the salt of the alpha-sulfo fatty acid is within the range of from 50 to 65% by weight.

* * * * *